United States Patent
Wang et al.

(10) Patent No.: US 10,946,026 B2
(45) Date of Patent: *Mar. 16, 2021

(54) PHARMACEUTICAL COMPOSITIONS AND METHODS FOR TREATING MENTAL, BEHAVIORAL, COGNITIVE DISORDERS

(71) Applicant: LA PharmaTech Inc., Blacksburg, VA (US)

(72) Inventors: Jianmin Wang, Blacksburg, VA (US); Geping Cui, Beijing (CN)

(73) Assignee: LA PharmaTech Inc., Blacksburg, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/424,788

(22) Filed: May 29, 2019

(65) Prior Publication Data
US 2020/0323868 A1 Oct. 15, 2020

Related U.S. Application Data

(63) Continuation of application No. 16/382,885, filed on Apr. 12, 2019.

(51) Int. Cl.
| | | |
|---|---|---|
| A61K 31/55 | (2006.01) | |
| A61P 25/28 | (2006.01) | |
| A61K 9/00 | (2006.01) | |
| A61K 31/13 | (2006.01) | |
| A61P 25/16 | (2006.01) | |

(52) U.S. Cl.
CPC ............ *A61K 31/55* (2013.01); *A61K 9/0053* (2013.01); *A61K 31/13* (2013.01); *A61P 25/16* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 5,068,233 | A | 11/1991 | Achterrath-Tuckerman et al. |
| 5,086,050 | A | 2/1992 | Hettche et al. |
| 5,994,357 | A | 11/1999 | Theoharides |
| 6,017,909 | A | 1/2000 | Hettche et al. |
| 6,849,621 | B2 | 2/2005 | Rosenblum et al. |
| 7,022,687 | B1 | 4/2006 | Szelenyi et al. |
| 7,220,735 | B2 | 5/2007 | Ting et al. |
| 7,355,042 | B2 | 4/2008 | Edgar et al. |
| 7,615,550 | B2 | 11/2009 | Heightman et al. |
| 7,786,161 | B2 | 8/2010 | Tani et al. |
| 8,071,073 | B2 | 12/2011 | Dang et al. |
| 8,168,620 | B2 | 5/2012 | Lulla et al. |
| 8,304,405 | B2 | 11/2012 | Lulla et al. |
| 8,318,709 | B2 | 11/2012 | Lulla et al. |
| 8,741,319 | B2 | 6/2014 | Crain et al. |
| 8,758,816 | B2 | 6/2014 | Fuge et al. |
| 8,859,531 | B2 | 10/2014 | Lee et al. |
| 8,865,733 | B2 | 10/2014 | Felder |
| 9,278,092 | B2 | 3/2016 | Chase et al. |
| 9,901,585 | B2 | 2/2018 | Lulla et al. |
| 9,919,050 | B2 | 3/2018 | Dang et al. |
| 10,639,314 | B1 | 5/2020 | Wang et al. |
| 10,639,315 | B1 | 5/2020 | Wang et al. |
| 10,639,316 | B1 | 5/2020 | Wang et al. |
| 2004/0006072 | A1 | 1/2004 | Franz et al. |
| 2006/0051416 | A1* | 3/2006 | Rastogi ............... A61K 9/2054 424/468 |
| 2009/0318703 | A1 | 12/2009 | Tani et al. |
| 2010/0152108 | A1 | 6/2010 | Hung et al. |
| 2014/0127328 | A1 | 5/2014 | Crain et al. |
| 2014/0158117 | A1 | 6/2014 | Dang et al. |
| 2015/0216849 | A1* | 8/2015 | Dedhiya ............... A61K 31/445 514/317 |
| 2017/0035780 | A1 | 2/2017 | Lulla et al. |
| 2018/0116979 | A1 | 5/2018 | Clarence-Smith et al. |
| 2020/0323867 | A1 | 10/2020 | Wang et al. |
| 2020/0323870 | A1 | 10/2020 | Wang et al. |
| 2020/0323871 | A1 | 10/2020 | Wang et al. |
| 2020/0323873 | A1 | 10/2020 | Wang et al. |
| 2020/0323876 | A1 | 10/2020 | Wang et al. |
| 2020/0323877 | A1 | 10/2020 | Wang et al. |

FOREIGN PATENT DOCUMENTS

| | | |
|---|---|---|
| WO | 2006058022 A1 | 6/2006 |
| WO | 2007061454 A1 | 5/2007 |
| WO | 2014018563 A3 | 5/2014 |
| WO | 2020209872 A1 | 10/2020 |

OTHER PUBLICATIONS

Aricept, Generic Name: donepezil hydrochloride, Brand Name: Aricept, Drug Description, RxList.com, Jan. 3, 2019.
Bezprozvanny, Ilya. The rise and fall of Dimebon. National Institute of Health. Feb. 12, 2014.
Category H1 receptor antagonists. Wikipedia. Sep. 20, 2012.
Co-Pending U.S. Appl. No. 16/382,885, Response to restriction requirement dated Oct. 2, 2019, 3pgs.
Co-Pending U.S. Appl. No. 16/382,885, Restriction Requirement dated Aug. 9, 2019, 7 pgs.
Co-Pending U.S. Appl. No. 16/398,845, Non-Final Office Action dated Aug. 6, 2019, 25 pages.
Co-Pending U.S. Appl. No. 16/398,845, Response to Non-Final Office Action dated Nov. 6, 2019, 9 pages.
Co-Pending U.S. Appl. No. 16/418,614, Non-Final Office Action dated Aug. 6, 2019, 31 pages.
Co-Pending U.S. Appl. No. 16/418,614, Response to Non-Final Office Action dated Nov. 6, 2019, 10 pages.
Co-Pending U.S. Appl. No. 16/426,121, Non-Final Office Action dated Aug. 6, 2019, 25 pages.
Co-Pending U.S. Appl. No. 16/426,121, Response to Non-Final Office Action dated Nov. 6, 2019, 9 pages.

(Continued)

*Primary Examiner* — Leslie A. Royds Draper
(74) *Attorney, Agent, or Firm* — New River Valley IP Law, PC; Michele L. Mayberry

(57) ABSTRACT

A pharmaceutical composition containing the therapeutically active ingredients of azelastine or a pharmaceutically acceptable salt of azelastine and memantine or a pharmaceutically acceptable salt of memantine is disclosed. A method of using the pharmaceutical composition for treating patients suffering from mental, behavioral, cognitive disorders is also disclosed.

18 Claims, No Drawings

(56) References Cited

OTHER PUBLICATIONS

Co-pending application No. PCT/US19/29885 International Search Report dated Jul. 15, 2019. 7 pages.
Co-pending application No. PCT/US19/33359 International Search Report and Written Opinion dated Aug. 15, 2019. 9 pages.
Co-Pending Application No. PCT/US2019/027293, Search Report & Written Opinion, dated Sep. 17, 2019, 8 pages.
Hansen et al. Clinical Interventions in Aging 2008, vol. 3, No. 2, pp. 211-225.
Hatakeyama, AikO, Masahiko Fujii, Reiko Hatakeyama, Yumiko Fukuoka, Takuma Satoh-Nakagawa and Hidetada Sasaki, Azelastine hydrochloride on behavioral and psychological symptoms and activities of daily living in dementia patients, Geriatr Gerontol Int 2008; 8: 59-61 (2008).
Naddafi, F., Mirshafiey A., The neglected role of histamine in Alzheimer's disease., Jun. 2013;28(4):327-36. doi: 10.1177/1533317513488925. Epub May 15, 2013.
Riethmuller et al. Arzneimittel-Forschung, 1994, vol. 44, No. 10, pp. 1136-1140.
Sedeyn, Jonathan Histamine Induces Alzheimer's Disease-Like Blood Brain Barrier Breach and local cellular Responses in Mouse Brain Organotypic Culture. Hindawi. Aug. 21, 2015.
St-Jean, Genevieve; Turcotte, Isabelle; Bastien, Celyne H. Cerebral asymmetry in insomnia sufferers. Frontiers in Neurology 2012, 3, 1-12.
Co-Pending U.S. Appl. No. 16/382,885, Response to Jun. 5, 2020 Final office action filed Jul. 31, 2020, 9 pages.
(Wang, Jianmin) Co-Pending U.S. Appl. No. 16/382,885, filed Apr. 12, 2019, Specification and claims.
(Wang, Jianmin) Co-Pending U.S. Appl. No. 16/398,845, filed Apr. 30, 2019, Specification and Claims.
(Wang, Jianmin) Co-Pending U.S. Appl. No. 16/418,614, filed May 21, 2019, Specification and Claims.
(Wang, Jianmin) Co-Pending U.S. Appl. No. 16/426,121, filed May 30, 2019, Specification and Claims.
(Wang, Jianmin) Co-Pending Application No. PCT/US19/29885, Filed Apr. 30, 2019, Specification and Claims.
(Wang, Jianmin) Co-Pending Application No. PCT/US19/33359, Filed May 21, 2019, Specification and Claims.
(Wang, Jianmin) Co-Pending Application No. PCT/US2019/027293, filed Apr. 12, 2019, Specification and Claims.
Co-Pending U.S. Appl. No. 16/382,885, Non-Final office action and list of references dated Nov. 29, 2019, 23 pgs.
Co-Pending U.S. Appl. No. 16/382,885, Response to Nov. 29, 2019 Non-Final office action filed Mar. 2, 2020.
Co-Pending U.S. Appl. No. 16/418,614, Notice of Allowance dated Jan. 30, 2020, 12 pages.
Co-Pending U.S. Appl. No. 16/426,121, Notice of allowance dated Jan. 21, 2020, 18 pages.
(Wang, Jianmin) Co-Pending U.S. Appl. No. 16/831,330, filed Mar. 26, 2020, Specification and Claims.
(Wang, Jianmin) Co-Pending U.S. Appl. No. 16/834,146, filed Mar. 30, 2020, Specification and Claims.
(Wang, Jianmin) Co-Pending U.S. Appl. No. 16/884,459, filed May 27, 2020, Specification and Claims.
(Wang, Jianmin) Co-Pending U.S. Appl. No. 16/884,553, filed May 27, 2020, Specification and Claims.
(Wang, Jianmin) Co-Pending U.S. Appl. No. 16/913,927, filed Jun. 26, 2020, Specification and Claims.
(Wang, Jianmin) Co-Pending Application No. PCT/US20/39916, Filed Jun. 26, 2020, Specification and Claims.
Casale, T. B. The interaction of azelastine with human lung histamine H1, beta, and muscarinic receptor-binding sites. J Allergy Clin Immunol. 1989;83:771-776.
Ciprandi, G., Pronzato, C., Passalacqua, G., et al. Topical azelastine reduces eosinophil activation and intercellular adhesion molecule-1 expression on nasal epithelial cells: An antiallergic activity. J Allergy Clin. Immunol. 1996;98(6 Pt 1):1088-1096.
Co-Pending U.S. Appl. No. 16/382,885, Final office action dated Jun. 5, 2020, 13 pgs.
Co-Pending U.S. Appl. No. 16/398,845, Interview Summary dated Dec. 18, 2019, 7 pages.
Co-Pending U.S. Appl. No. 16/398,845, Notice of Allowance dated Jan. 21, 2020, 11 pages.
Co-Pending U.S. Appl. No. 16/418,614, Interview Summary dated Dec. 18, 2019, 7 pages.
Goedert, M., Spillantini, M.G,. 2006. A century of Alzheimer's disease. Science, 314:777-81.
Hazama, H., Nakajima, T., Hisada, T., Hamada, E., Omata, M., Kurachi, Y. Effects of azelastine on membrane currents in tracheal smooth muscle cells isolated from the guinea-pig. Eur J Pharmacol. 1994;259: 143-150.
Kempuraj, Duraisamy, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231—Nov. 9, 2003.
Simons, F.E., Simons, K.J. Clinical pharmacology of new histamine H1 receptor antagonist. Clin Pharmacokinet. 1999;36:329-352.
Szelenyi, L, Achterrath-Tuckermann, U., Schmidt, J., Minker, E, Paegelow, I., Werner, H. Azelastine: A multifaceted drug for asthma therapy. Agents Actions Suppl. 1991;34:295-311. (abstract).
Tanaka, Hibiki, Hashimoto, Mamoru, et al, 2015. Relationship Between Dementia Severity and Behavioural and Psychological Symptoms in Early-Onset Alzheimer's Disease. Psychogeriatrics. Dec. 2015;15(4):242-7.
Williams, Patricia B, Crandall, Elizabeth, and Sheppard, John D, 2010, Azelastine hydrochloride, a dual-acting anti-inflammatory ophthalmic solution, for treatment of allergic conjunctivitis. Clinical Ophthalmology 2010:4 993-1001.
Yoneda, Kazunori, et al. 1997, Suppression by Azelastine Hydrochloride of NF-KB Activation Involved in Generation of Cytokines and Nitric Oxide. Japanese Journal of Pharmacology, 73: 145-53.
(Wang, Jianmin) Co-Pending U.S. Appl. No. 17/094,405, filed Nov. 10, 2020, Specification and Claims.
(Wang, Jianmin) Co-Pending Application No. PCT/US20/34737, filed May 27, 2020, Specifications and Claims.
(Wang, Jianmin) Co-Pending Application No. PCT/US20/59846, filed Nov. 10, 2020, Specifications and figures.
Co-Pending U.S. Appl. No. 16/426,12, Interview Summary dated Dec. 18, 2019, 7 pages.
Co-Pending U.S. Appl. No. 16/884,459, Non-Final Office Action dated Aug. 11, 2020, 35 pages.
Co-Pending U.S. Appl. No. 16/884,459, Response to Aug. 11, 2020 Non-Final Office Action dated Nov. 12, 2020, 11 pages.
Co-Pending U.S. Appl. No. 16/884,553, Non-Final Office Action dated Aug. 11, 2020, 26 pages.
Co-Pending U.S. Appl. No. 16/884,553, Response to Aug. 11, 2020 Non-Final Office Action dated Nov. 12, 2020, 8 pages.
Co-Pending U.S. Appl. No. 16/913,927, Non-Final Office Action dated Nov. 9, 2020, 24 pages.
Co-Pending U.S. Appl. No. 16/913,927, Response to Aug. 27, 2020 Restriction Requirement, dated Oct. 20, 2020, 5 pages.
Co-Pending U.S. Appl. No. 16/913,927, Restriction Requirement dated Aug. 27, 2020, 5 pages.
Co-Pending Application No. PCT/US20/34735, International Search Report and Written Opinion dated Aug. 17, 2020, 10 pages.
Co-Pending Application No. PCT/US20/39916, International Search Report and Written Opinion dated Oct. 8, 2020, 8 pages.
Co-Pending Application No. PCT/US2019/027293, Corrected Written Opinion, dated Oct. 29, 2019, 5 pages.
Galatowicz, G, Ajayi Y, Stern ME, Calder VL. Ocular antiallergic compounds selectively inhibit human mast cell cytokines in vitro and conjunctival cell infiltration in vivo. Clin Exp Allergy. 2007; 37:1648-1656.
Hashiro et al. "A Combination Therapy of Psychotropic Drugs and Antihistaminics or Antiallergics in Patients with Chronic Urticaria". Journal of Dermatological Sciences, 1996; 11:209-213.
Co-Pending U.S. Appl. No. 16/884,553, Notice of Allowance dated Dec. 2, 2020, 9 pages.

(56) References Cited

OTHER PUBLICATIONS

Co-Penidng U.S. Appl. No. 16/382,885, Non-Final office action dated Dec. 22, 2020, 10 pgs.

* cited by examiner

PHARMACEUTICAL COMPOSITIONS AND METHODS FOR TREATING MENTAL, BEHAVIORAL, COGNITIVE DISORDERS

CROSS-REFERENCE TO RELATED APPLICATIONS

The present application is a Continuation application of U.S. patent application Ser. No. 16/382,885 filed on Apr. 12, 2019, the disclosure of which is hereby incorporated by reference herein in its entirety.

FIELD OF THE INVENTION

The invention relates to the field of practical medicine, namely, to the combined use of pharmaceutical compositions exhibiting a neurotropic action, alleviating manifestations of mental, behavioral, cognitive disorders in cases of organic damage of various origin to the central nervous system.

BACKGROUND OF THE INVENTION

Alzheimer's disease (AD) is a progressive, chronic neurodegenerative disease that usually starts slowly and gradually worsens over time. Alzheimer's is the most common cause of dementia among older adults. Dementia is the loss of cognitive functioning—thinking, remembering, and reasoning—and behavioral abilities to such an extent that it interferes with a person's daily life and activities. In its early stages, memory loss is mild, but with late-stage AD, individuals lose the ability to carry on a conversation and respond to their environment. If untreated, AD ultimately leads to death. Although the speed of progression can vary, the typical life expectancy following diagnosis is three to nine years.

A central mechanism in learning and memory is long-term potentiation (LTP). LTP is mediated by the neurotransmitter glutamate via the NMDA receptor. The NMDA receptors can be found diffusely throughout the brain. However, they densely populate the dendrites of pyramidal cells in the hippocampus and cortex (areas known to be involved in cognition, learning, and memory). In addition to the relationship between LTP and learning, elevated glutamate levels are associated with excitotoxicity. Chronic low-dose administration of NMDA receptor agonists has been shown to induce apoptosis, while high doses induce necrosis. The activation of glutamate receptors has also been found to induce the release of glutamate. Thus, a large build-up of glutamate can occur and induce a massive accumulation of $Ca^{2+}$, leading to apoptosis. It was also noted that amyloid-beta (AB) plaques increase a neuron's vulnerability to excitotoxicity. AB plaques, a pathological feature of AD, were found to induce depolarization of astrocytes, extracellular accumulation of glutamate, and intracellular deposition of $Ca^{2+}$. Therefore, the glutamate-induced excitotoxicity pathway made an excellent target for the therapy of AD.

Under physiologic conditions, the glutamate released by neurons is metabolized or taken up by neighboring cells. When these pathways are disrupted, the accumulated glutamate overexcites the NMDA receptor and induces pathology characteristic of neurodegenerative diseases. NMDA receptors act as a calcium [II] ion ($Ca^{2+}$) channel that activates when bound by glycine, glutamate, and/or NMDA. However, the channel functions only when the cell membrane is depolarized due to the blockade of the channel by the magnesium [II] ion ($Mg^{2+}$). This prevents the influx of $Ca^{2+}$ when the neuron is at rest. Under pathological conditions, such as a chronically depolarized membrane, $Mg^{2+}$ leaves the channel and neuronal metabolism is inhibited, leading to cell death. When this happens, the $Ca^{2+}$ influx is unrestricted for a longer period of time than normal. This influx of $Ca^{2+}$ contributes to an alteration of cell function, leading to cell death either through free radicals or through overload of the mitochondria, resulting in free radical formation, caspase activation, and the release of apoptosis-inducing factors. Antagonists to the NMDA vary in affinity and in site of action, resulting in different alterations to the channel. Regardless of the mechanism of action, antagonists decrease the permeability of the channel and prevent an influx of $Ca^{2+}$. Thus, NMDA receptor antagonists are looked to as possible neuroprotective agents and potential therapies for neurodegenerative disease.

Most NMDA antagonists are competitive antagonists and are not well tolerated by patients due to side effects, which can include hallucinations and schizophrenia-type symptoms. The side effects likely result from the competitive antagonists blocking physiological functions of the NMDA receptor. Its role in cognition, memory, and learning make it necessary that any drug using the NMDA receptor as a target of action must preserve physiologic function to be therapeutically useful. Memantine acts on activated NMDA receptors by binding to a site located in the channel of the receptor.

Memantine is a fast-binding antagonist which binds to the channel in a pseudo-first order manner. However, it also dissociates from the receptor quickly and in a concentration independent manner. This allows the dose to affect the binding of memantine without affecting its removal from the site of action and allowing for increased potency with minimal side effects. In comparison with other antagonists, memantine has a much faster course of action and thus has less effect on physiologic mechanisms. For this reason, memantine offers a lot of promise in the therapy of neurodegenerative disease because it will preserve physiological function. In addition, the uncompetitive nature of memantine's mechanism of action makes its antagonistic activity more potent in areas with massive activation of NMDA receptors. Memantine's mechanism of action is also voltage-dependent, which leads to the removal of the memantine blockage by depolarization of the membrane. All of these characteristics make memantine a strong candidate for treating pathology induced by excitotoxicity. In several studies, memantine was found to prevent neuronal death induced via excitotoxic mechanisms.

However, memantine will not cure AD or prevent the loss of these abilities at some time in the future. So, AD has no current cure, and our effort is to find better ways to reverse the disease, delay and prevent it from developing.

On the other hand, the genetic, cellular, and molecular changes associated with AD support the evidence that activated immune and inflammatory processes is a part of the disease. Also, a strong benefit of long-term use of NSAIDs was shown in epidemiological studies. So, it is generally accepted that AD is partially an inflammatory disease and that inhibiting inflammation is an option of treating AD.

Inflammation clearly occurs in pathologically vulnerable regions of the AD brain, and it does so with the full complexity of local peripheral inflammatory responses. In the periphery, degenerating tissue and the deposition of highly insoluble abnormal materials are classical stimulants of inflammation. Likewise, in the AD brain damaged neurons and neurites and highly insoluble amyloid β peptide deposits and neurofibrillary tangles provide obvious stimuli for inflammation. Because these stimuli are discrete, micro-localized, and present from early preclinical to terminal stages of AD, local upregulation of complement, cytokines, acute phase reactants, and other inflammatory mediators is also discrete, micro-localized, and chronic. Cumulated over many years, direct and bystander damage from AD inflammatory mechanisms is likely to significantly exacerbate the very pathogenic processes that gave rise to it. Thus, animal models and clinical studies so far strongly suggest that AD inflammation significantly contributes to AD pathogenesis. By better understanding AD inflammatory and immune-regulatory processes, it should be possible to develop anti-inflammatory approaches that may reverse or delay or prevent developing of this devastating disorder.

Azelastine is classified pharmacologically as a second generation antihistamine and is a relatively selective, non-sedating, competitive antagonist at H1 receptors. More uniquely, its inhibition of inflammatory mediators, in addition to antihistaminic and mast cell stabilizing effects, places it among the new generation of dual-acting anti-inflammatory drugs. In addition to azelastine's high affinity for H1 receptors, its ability to modify several other mediators of inflammation and allergy contributes to its mechanism of action. In vitro and in vivo studies, as well as clinical trials support the dual effects of direct inhibition and stabilization of inflammatory cells. In vitro data indicate that azelastine's affinity for H1 receptors is estimated to be several times greater than that of chlorpheniramine, a first-generation H1 antagonist. Azelastine has only weak affinity for H2 receptors. Release of histamine from mast cells is also inhibited possibly by reversible inhibition of voltage-dependent L-type calcium channels. Inhibition of mast cell degranulation may also decrease the release of other inflammatory mediators, including leukotrienes and interleukin-1β, among others. Azelastine also directly antagonizes other mediators of inflammation, such as tumor necrosis factor-α, leukotrienes, endothelin-1, and platelet-activating factor.

SUMMARY OF THE INVENTION

The present invention includes a pharmaceutical composition that comprises two active ingredients and one or more pharmaceutically acceptable excipients. This pharmaceutical composition comprises the first active ingredient that is azelastine or a pharmaceutically acceptable salt of azelastine and the second active ingredient that is memantine or a pharmaceutically acceptable salt of memantine.

In some embodiments of this invention, the pharmaceutically acceptable salt of azelastine in the pharmaceutical composition is azelastine hydrochloride and the pharmaceutically acceptable salt of memantine in this pharmaceutical composition is memantine hydrochloride.

In some embodiments of this invention, azelastine hydrochloride (and/or other salt thereof) in the pharmaceutical composition is provided in an amount of about 1 mg to about 20 mg and/or memantine hydrochloride (and/or other salt thereof) in this pharmaceutical composition is in an amount of about 1 mg to about 30 mg.

The present invention also includes an oral pharmaceutical dosage form of the pharmaceutical composition that is a solid form or a liquid form.

The present invention further includes the medical use of the oral pharmaceutical dosage form of the pharmaceutical composition through administration of the dosage form to patients with a neurodegenerative disorder such as Alzheimer's disease, vascular dementia, or Parkinson's disease.

In some embodiments of this invention, an oral pharmaceutical dosage form of the pharmaceutical composition containing azelastine hydrochloride (and/or other salt thereof) in an amount of about 6 mg to about 12 mg and/or memantine hydrochloride (and/or other salt thereof) of in an amount of about 2 mg to about 6 mg is administered to patients with late stage Alzheimer's disease

DETAILED DESCRIPTION OF THE INVENTION

The inventors of the present invention surprisingly found that a pharmaceutical composition with an oral dosage form comprising the active agents, a salt form of azelastine and a salt form of memantine, is suitable for treating patients suffering from mental, behavioral, cognitive disorders.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Mental, behavioral, cognitive disorders can include but are not limited to Alzheimer's disease, dementia, Parkinson's disease, Huntington's disease and combinations of any thereof and other neurodegenerative disorders.

As used herein, the term "memantine" refers to memantine free base, 1-Amino-3,5-dimethyladamantane, 1,3-Dimethyl-5-adamantanamine, 3,5-Dimethyl-1-adamantanamine, or 3,5-Dimethyltricyclo(3.3.1.1(3,7))decan-1-amine. In certain embodiments, memantine also includes any pharmaceutically acceptable salt, such as the hydrochloride or HCl salt. Preferably, in any embodiments of the invention as described herein, the memantine is in the form of its hydrochloride salt, as memantine hydrochloride or memantine HCl. More preferably, in any embodiment of the invention as described herein, reference to the amounts and dosage ranges of memantine in oral dosage forms are to the amounts and dosage ranges of memantine hydrochloride.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine in the solid oral dosage forms are to the amounts and dosage ranges of azelastine hydrochloride.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to effect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be via capsule, tablet, or the like.

The term "about" used herein in the context of quantitative measurements means the indicated amount ±10%. For example, with a ±10% range, "about 5 mg" can mean 4.5-5.5 mg.

The pharmaceutical composition may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration. For example, admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Capsules may be formulated by mixing the compound with a pharmaceutical diluent which is inert and inserting this mixture into a hard gelatin capsule having the appropriate size. If soft capsules are desired, a slurry of the compound with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure are usually administered orally. This disclosure therefore provides pharmaceutical compositions that comprise a solid dispersion comprising azelastine and memantine as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutical composition may further comprise pharmaceutical excipients such as diluents, binders, fillers, glidants, disintegrants, lubricants, solubilizers, and combinations thereof. Some examples of suitable excipients are described herein. When the pharmaceutical composition is formulated into a tablet, the tablet may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In embodiments, the pharmaceutical composition can comprise a) about 1 mg-50 mg of azelastine HCl (and/or other salt thereof) and/or b) about 1 mg to 70 mg of memantine HCl (and/or other salt thereof) or a) about 2 mg-20 mg of azelastine HCl (and/or other salt thereof) and/or b) about 2 mg to 30 mg of memantine HCl (and/or other salt thereof) or a) about 8 mg-16 mg of azelastine HCl (and/or other salt thereof) and/or b) about 2 mg to 5 mg of memantine HCl (and/or other salt thereof). For example, the composition can comprise a) about 12 mg of azelastine HCl (and/or other salt thereof) and/or b) about 3 mg of memantine HCl (and/or other salt thereof). Further, for example, compositions of the invention can comprise azelastine or a pharmaceutically acceptable salt of azelastine present in an amount in the range of about 1 mg to about 50 mg and/or memantine or a pharmaceutically acceptable salt of memantine present in an amount in the range of about 1 mg to about 70 mg. In embodiments, the amount of azelastine HCl (and/or other salt thereof) present in the composition can be equal to, more than, or less than the amount of memantine HCl (and/or other salt thereof) present in the composition. In embodiments, the amount of azelastine HCl (and/or other salt thereof) present in the composition can be 2 times as much, or 3 times as much, or 4, 5, 6, 7, 8, 9, 10, 15, 20, 25, 30, 35, 40, 45, 50, 75, 100, or 1,000 times as much as the amount of memantine HCl (and/or other salt thereof) present in the composition, or vice versa. Any one or more of the compositions of the invention can be used with any one or more the methods of the invention disclosed herein, or other methods of using the compositions.

It will be understood, that the amount of the pharmaceutical composition containing azelastine HCl and memantine HCl actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing azelastine HCl and memantine HCl as described herein are administered to a patient suffering from a neurodegenerative disorder, such as Alzheimer's disease, by oral administration once daily, twice daily, once every other day, two times a week, three times a week, four times a week, or five times a week.

In embodiments, the pharmaceutical dosage forms and tablets of pharmaceutical compositions containing azelastine HCl and memantine HCl as described herein are effective in reversing symptoms in patients with late stage Alzheimer's disease in about 6-24 weeks.

The following Examples are illustrative and should not be interpreted to limit the scope of the claimed subject matter.

Example 1

A 79 year old female with a weight of 51 kilograms was diagnosed with late stage Alzheimer's disease and treated with memantine (10 mg) for 5 years. But her memory and cognitive skills continued to worsen. She could barely remember anything and could only speak a few words. She eventually had a round-the-clock assistance with her daily activities and personal caring. She couldn't walk for more than 10 steps even with assistance. At this stage, she started a treatment with liquid oral form of the claimed pharmaceutical composition containing 12 mg of azelastine HCl and 5 mg of memantine HCl once daily. After only a month and half, with assistance she could walk. After 3 months, she had facial and eye expression and could talk for a few minutes and walked with only light assistance. After 6 months of the treatment, she could talk freely and sang songs and could walk independently. During the 6-month treatment, her weight increased by 5 kilograms.

Example 2

An 81 year old female with a weight of 55 kilograms was diagnosed with late stage Alzheimer's disease. She had a round-the-clock assistance with her daily activities including personal care, eating, walking. She could only speak less than 5 words and had an irregular sleeping pattern. She was treated with a liquid oral form of the claimed pharmaceutical composition containing 12 mg of azelastine HCl and 5 mg of memantine HCl. After only a month and half, her round-the-clock assistance was reduced by around 50%. After 3 months, she could carry out her basic personal care activities herself and could speak more than 10 words.

Example 3

A 77 year old male with a weight of 66 kilograms was diagnosed with late stage Alzheimer's disease. He could only speak a few words. He had difficulty in sleeping. His personality was described as illogical or irrational, anxious or irritable, and aggressive or hostile. He was uncooperative most of time. He needed light assistance with walking. He was monitored by an assistant round-the-clock. He was treated with tablets of the pharmaceutical composition containing 14 mg of azelastine HCl and 5 mg of memantine HCl. After a month and half, his personality was described as more rational, with much less aggression with no hostility. After 3 months, he could sleep regularly and he no longer needed round-the-clock assistance. He could speak for more than 1 minute.

REFERENCES

Dreyer E B, Zhang D, Lipton S A. Transcriptional or translational inhibition blocks low dose NMDA-mediated cell death. Neuroreport. 1995; 6(6):942-944.

Bonfoco E, Krainc D, Ankarcrona M, Nicotera P, Lipton S A. Apoptosis and necrosis: two distinct events induced, respectively, by mild and intense insults with N-methyl-D-aspartate or nitric oxide/superoxide in cortical cell cultures. Proc Natl Acad Sci USA. 1995; 92(16):7162-7166.

Sucher N J, Lipton S A, Dreyer E B. Molecular basis of glutamate toxicity in retinal ganglion cells. Vision Res. 1997; 37(24):3483-3493.

Koh J Y, Yang L L, Cotman C W. Beta-amyloid protein increases the vulnerability of cultured cortical neurons to excitotoxic damage. Brain Res. 1990; 533(2):315-320.

Harkany T, Abraham I, Timmerman W, et al. Beta-amyloid neurotoxicity is mediated by a glutamate-triggered excitotoxic cascade in rat nucleus basalis. Eur J Neurosci. 2000; 12(8):2735-2745.

Zeevalk G D, Nicklas W J. Evidence that the loss of the voltage-dependent Mg2+ block at the N-methyl-D-aspartate receptor underlies receptor activation during inhibition of neuronal metabolism. J Neurochem. 1992; 59(4):1211-1220.

Lipton S A, Nicotera P. Calcium, free radicals and excitotoxins in neuronal apoptosis. Cell Calcium. 1998; 23:2-3.165-171.

Lipton S A. Paradigm shift in neuroprotection by NMDA receptor blockade: memantine and beyond. Nat Rev Drug Discov. 2006; 5(2):160-170.

Chen H S, Lipton S A. Mechanism of memantine block of NMDA-activated channels in rat retinal ganglion cells. J Physiol. 1997; 499(Pt 1):27-49.

Chen H S, Pellegrini J W, Aggarwal S K, et al. Open-channel block of N-methyl-D-aspartate (NMDA) responses by memantine: therapeutic advantage against NMDA receptor-mediated neurotoxicity. J Neurosci. 1992; 12(11):4427-4436.

Bresink I, Benke T A, Collett V J, et al. Effects of memantine on recombinant rat NMDA receptors expressed in HEK 293 cells. Br J Pharmacol. 1996; 119(2):195-204.

Vorwerk C K, Lipton S A, Zurakowski D, Hyman B T, Sabel B A, Dreyer E B. Chronic low-dose glutamate is toxic to retinal ganglion cells. Toxicity blocked by memantine. Invest Ophthalmol Vis Sci. 1996; 37(8):1618-1624.

Pellegrini J W, Lipton S A. Delayed administration of memantine prevents N-methyl-D-aspartate receptor-mediated neurotoxicity. Ann Neurol. 1993; 33(4):403-407.

Gelosa P, Colazzo F, Tremoli E, Sironi L, Castiglioni L. Cysteinyl Leukotrienes as Potential Pharmacological Targets for Cerebral Diseases. Mediators Inflamm. 2017 May 10.

Alzheimer's Disease International, "World Alzheimer Report 2010: the global economic impact of dementia."

G. T. Grossberg, V. Pejović, M. L. Miller, and S. M. Graham, "Memantine therapy of behavioral symptoms in community-dwelling patients with moderate to severe Alzheimer's disease," Dementia and Geriatric Cognitive Disorders, vol. 27, no. 2, pp. 164-172, 2009.

National Institute for Clinical Excellence (NICE), "Donepezil, galantamine, rivastigmine and memantine for the treatment of Alzheimer's disease," NICE Technology Appraisal Guidance 217, National Institute for Clinical Excellence, London, UK, 2011, Institute for Quality and Efficiency in Health Care (IQWiG) and Federal Joint Committee, "Responder analyses on memantine in Alzheimer's disease," Executive Summary of Rapid Report A 10-06, Institute for Quality and Efficiency in Healthcare (IQWiG), 2011.

B. Winblad, R. W. Jones, Y. Wirth, A. Stöffler, and H. J. Möbius, "Memantine in moderate-to-severe Alzheimer's disease: a meta-analysis of randomised clinical trials," Dementia and Geriatric Cognitive Disorders, vol. 24, no. 1, pp. 20-27, 2007.

S. J. Thomas and G. T. Grossberg, "Memantine: a review of studies into its safety and efficacy in treating Alzheimer's disease and other dementias," Clinical Interventions in Aging, vol. 4, pp. 367-377, 2009.

R. S. Doody, J. K. Dunn, C. M. Clark et al., "Chronic donepezil treatment is associated with slowed cognitive decline in Alzheimer's disease," Dementia and Geriatric Cognitive Disorders, vol. 12, no. 4, pp. 295-300, 2001.

A. Clegg, J. Bryant, T. Nicholson et al., "Clinical and cost-effectiveness of donepezil, rivastigmine and galantamine for Alzheimer's disease: a rapid and systematic review," Health Technology Assessment, vol. 5, no. 1, pp. 1-137, 2001.

R. A. Hansen, G. Gartlehner, A. P. Webb, L. C. Morgan, C. G. Moore, and D. E. Jonas, "Efficacy and safety of donepezil, galantamine, and rivastigmine for the treatment of Alzheimer's disease: a systematic review and meta-analysis," Clinical Interventions in Aging, vol. 3, no. 2, pp. 211-225, 2008.

D. D. Christensen, "Higher-dose (23 mg/dayay) donepezil formulation for the treatment of patients with moderate-to-severe Alzheimer's disease," Postgraduate Medicine, vol. 124, no. 6, pp. 110-116, 2012.

J. L. Cummings, D. Geldmacher, M. Farlow, M. Sabbagh, D. Christensen, and P. Betz, "High-dose donepezil (23 mg/day) for the treatment of moderate and severe Alzheimer's disease: drug profile and clinical guidelines," CNS Neuroscience & Therapeutics, vol. 19, no. 5, pp. 294-301, 2013.

S. Ferris, J. Cummings, D. Christensen et al., "Effects of donepezil 23 mg on Severe Impairment Battery domains in patients with moderate-to-severe Alzheimer's disease: evaluating the impact of baseline severity," Alzheimer's Research & Therapy, vol. 5, no. 1, article 12, 2013.

A. Atri, J. L. Molinuevo, O. Lemming, Y. Wirth, I. Pulte, and D. Wilkinson, "Memantine in patients with Alzheimer's disease receiving donepezil: new analyses of efficacy and safety for combination therapy," Alzheimer's Research & Therapy, vol. 5, no. 1, article 6, 2013.

S. Gauthier and J. L. Molinuevo, "Benefits of combined cholinesterase inhibitor and memantine treatment in moderate-severe Alzheimer's disease," Alzheimer's & Dementia, vol. 9, no. 3, pp. 326-331, 2013.

G. Wells, B. Shea, D. O'Connell et al., The Newcastle-Ottawa Scale (NOS) for Assessing the Quality of Nonrandomized Studies in Metaanalysis, Ottawa Hospital Research Institute, Ottawa, Canada, 2011.

C. Fox, M. Crugel, I. Maidment et al., "Efficacy of memantine for agitation in Alzheimer's dementia: a randomised double-blind placebo controlled trial," PLoS ONE, vol. 7, no. 5, Article ID e35185, 2012.

H. Förstl, S. S. Stamouli, W. Janetzky, A. Galanopoulos, C. Karageorgiou, and M. Tzanakaki, "Memantine in everyday clinical practice: a comparison of studies in Germany and Greece," Dementia and Geriatric Cognitive Disorders, vol. 32, no. 4, pp. 267-272, 2011.

N. Herrmann, J. Cappell, G. M. Eryavec, and K. L. Lancôtt, "Changes in nursing burden following memantine for agitation and aggression in long-term care residents with moderate to severe Alzheimer's disease: an open-label pilot study," CNS Drugs, vol. 25, no. 5, pp. 425-433, 2011.

J. B. Schulz, M. Rainer, H. Klünemann et al., "Sustained effects of once-daily memantine treatment on cognition and functional communication skills in patients with moderate to severe Alzheimer's disease: results of a 16-week open-label trial," Journal of Alzheimer's Disease, vol. 25, no. 3, pp. 463-475, 2011.

M. Rainer, A. Wuschitz, C. Jagsch, C. Erb, J.-J. Chirikdjian, and H. A. M. Mucke, "Memantine in moderate to severe Alzheimer's disease: an observational post-marketing study," Journal of Neural Transmission, vol. 118, no. 8, pp. 1255-1259, 2011.

G. K. Wilcock, C. G. Ballard, J. A. Cooper, and H. Loft, "Memantine for agitation/aggression and psychosis in moderately severe to severe Alzheimer's disease: a pooled analysis of 3 studies," Journal of Clinical Psychiatry, vol. 69, no. 3, pp. 341-348, 2008.

M. M. Carrasco, L. Agüera, P. Gil, A. Moriñigo, and T. Leon, "Safety and effectiveness of donepezil on behavioral symptoms in patients with Alzheimer disease," Alzheimer Disease and Associated Disorders, vol. 25, no. 4, pp. 333-340, 2011.

M. R. Farlow, S. Salloway, P. N. Tariot et al., "Effectiveness and tolerability of high-dose (23 mg/d) versus standard-dose (10 mg/d) donepezil in moderate to severe Alzheimer's disease: a 24-week, randomized, double-blind study," Clinical Therapeutics, vol. 32, no. 7, pp. 1234-1251, 2010.

M. Farlow, F. Veloso, M. Moline et al., "Safety and tolerability of donepezil 23 mg in moderate to severe Alzheimer's disease," BMC Neurology, vol. 11, article 57, 2011.

E. Schwam and Y. Xu, "Cognition and function in Alzheimer's disease: Identifying the transitions from moderate to severe disease," Dementia and Geriatric Cognitive Disorders, vol. 29, no. 4, pp. 309-316, 2010.

A. Homma, Y. Imai, H. Tago et al., "Donepezil treatment of patients with severe Alzheimer's disease in a Japanese population: results from a 24-week, double-blind, placebo-controlled, randomized trial," Dementia and Geriatric Cognitive Disorders, vol. 25, no. 5, pp. 399-407, 2008.

S. E. Black, R. Doody, H. Li et al., "Donepezil preserves cognition and global function in patients with severe Alzheimer disease," Neurology, vol. 69, no. 5, pp. 459-469, 2007.

R. Howard, R. McShane, J. Lindesay et al., "Donepezil and memantine for moderate-to-severe Alzheimer's disease," The New England Journal of Medicine, vol. 366, no. 10, pp. 893-903, 2012.

R. S. Doody, D. S. Geldmacher, M. R. Farlow, Y. Sun, M. Moline, and J. Mackell, "Efficacy and safety of donepezil 23 mg versus donepezil 10 mg for moderate-to-severe Alzheimer's disease: a subgroup analysis in patients already taking or not taking concomitant memantine," Dementia and Geriatric Cognitive Disorders, vol. 33, no. 2-3, pp. 164-173, 2012.

M. R. Farlow, M. L. Miller, and V. Pejovic, "Treatment options in Alzheimer's disease: maximizing benefit, managing expectations," Dementia and Geriatric Cognitive Disorders, vol. 25, no. 5, pp. 408-422, 2008.

A. K. Wallin, N. Andreasen, S. Eriksson et al., "Donepezil in Alzheimer's disease: what to expect after 3 years of treatment in a routine clinical setting," Dementia and Geriatric Cognitive Disorders, vol. 23, no. 3, pp. 150-160, 2007.

S. D. Rountree, W. Chan, V. N. Pavlik, E. J. Darby, S. Siddiqui, and R. S. Doody, "Persistent treatment with cholinesterase inhibitors and/or memantine slows clinical progression of Alzheimer disease," Alzheimer's Research & Therapy, vol. 1, no. 2, article 7, 2009.

D. Galasko, F. Schmitt, R. Thomas, S. Jin, D. Bennett, and S. Ferris, "Detailed assessment of activities of daily living in moderate to severe Alzheimer's disease," Journal of the International Neuropsychological Society, vol. 11, no. 4, pp. 446-453, 2005.

B. Winblad and N. Poritis, "Memantine in severe dementia: results of the MBest study (benefit and efficacy in severely demented patients during treatment with memantine)," International Journal of Geriatric Psychiatry, vol. 14, no. 2, pp. 135-146, 1999.

D. Wilkinson and H. F. Andersen, "Analysis of the effect of memantine in reducing the worsening of clinical symptoms in patients with moderate to severe Alzheimer's disease," Dementia and Geriatric Cognitive Disorders, vol. 24, no. 2, pp. 138-145, 2007.

D. Wilkinson, R. Schindler, E. Schwam et al., "Effectiveness of donepezil in reducing clinical worsening in patients with mild-to-moderate Alzheimer's disease," Dementia and Geriatric Cognitive Disorders, vol. 28, no. 3, pp. 244-251, 2009.

R. S. Doody, P. N. Tariot, E. Pfeiffer, J. T. Olin, and S. M. Graham, "Meta-analysis of six-month memantine trials in Alzheimer's disease," Alzheimer's and Dementia, vol. 3, no. 1, pp. 7-17, 2007.

F. A. Schmitt, C. H. van Dyck, C. H. Wichems, and J. T. Olin, "Cognitive response to memantine in moderate to severe Alzheimer disease patients already receiving donepezil: an exploratory reanalysis," Alzheimer Disease and Associated Disorders, vol. 20, no. 4, pp. 255-262, 2006.

O. L. Lopez, J. T. Becker, A. S. Wahed et al., "Long-term effects of the concomitant use of memantine with cholinesterase inhibition in Alzheimer disease," Journal of Neurology, Neurosurgery and Psychiatry, vol. 80, no. 6, pp. 600-607, 2009.

M. Bond, G. Rogers, J. Peters et al., "The effectiveness and cost effectiveness of donepezil, galantamine, rivastigmine and memantine for the treatment of Alzheimer's disease: a systematic review and economic model," NIHR HTA Programme Project Number 09/87/01, National Institute for Clinical Excellence, London, UK, 2010.

L. E. Farrimond, E. Roberts, and R. McShane, "Memantine and cholinesterase inhibitor combination therapy for Alzheimer's disease: a systematic review," BMJ Open, vol. 2, no. 3, 2012.

A. Atri, L. W. Shaughnessy, J. J. Locascio, and J. H. Growdon, "Long-term course and effectiveness of combination therapy in Alzheimer disease," Alzheimer Disease and Associated Disorders, vol. 22, no. 3, pp. 209-221, 2008.

A. Atri, S. D. Rountree, O. L. Lopez, and R. S. Doody, "Validity, significance, strengths, limitations, and evidentiary value of real-world clinical data for combination therapy in Alzheimer's disease: comparison of efficacy and effectiveness studies," Neurodegenerative Diseases, vol. 10, no. 1-4, pp. 170-174, 2012.

C. W. Zhu and M. Sano, "Economic considerations in the management of Alzheimer's disease," Clinical interventions in aging, vol. 1, no. 2, pp. 143-154, 2006.

Epstein A B, van Hoven P T, Kaufman A, Can W W. Management of allergic conjunctivitis: An evaluation of the perceived comfort and therapeutic efficacy of olopatadine 0.2% and azelastine 0.05% from two prospective studies. Clin Ophthalmol. 2009; 3:329-336.

Bielory L, Bielory B. Ocular allergy: An allergist's perspective. Aug. 16, 2010.

Pflugfelder S C. Prevalence, burden, and pharmacoeconomics of dry eye disease. Am J Manag Care. 2008; 14 Suppl 3:S102-S106.

Bielory L, Lien K W, Bigelsen S. Efficacy and tolerability of newer antihistamines in the treatment of allergic conjunctivitis. Drugs. 2005; 65:215-218.

Bielory L, Buddiga P, Bigelsen S. Ocular allergy treatment comparisons: Azelastine and olopatadine. Curr Allergy Asthma Rep. 2004; 4:320-325.

Baudouin C. Detrimental effect of preservative in eye drops: Implications for the treatment of glaucoma. Acta Ophthalmologica. 2008; 86:716-726.

Lee J S, Lee J E, Kim N, Oum B S. Comparison of the conjunctival toxicity of topical ocular antiallergic agents. J Ocul Pharmacol Ther. 2008; 24:557-562.

Lambiase A, Micera A, Bonini S. Multiple action agents and the eye: Do they really stabilize mast cells? Curr Opin Allergy Clin Immunol. 2009; 9:454-465.

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Perhach J L, Connell J T, Kemp J P. Treatment of upper and lower airway disease with azelastine. N Engl Reg Allergy Proc. 1987; 8:121-124.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

Loyd Allen, Ansel's Pharmaceutical Dosage Forms and Drug Delivery Systems, Tenth (2013)

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of treating a patient having Parkinson's disease, comprising:
   administering a pharmaceutical composition comprising:
   about 10-50 mg of azelastine or of a pharmaceutically acceptable salt of azelastine;
   memantine or a pharmaceutically acceptable salt of memantine; and
   one or more pharmaceutically acceptable excipients.

2. The method of claim 1, wherein the pharmaceutical composition is administered daily to the patient in an oral solid or liquid form.

3. The method of claim 2, wherein the azelastine or the pharmaceutically acceptable salt of azelastine is present in the pharmaceutical composition in an amount in the range of about 10 mg to about 20 mg daily.

4. The method of claim 2, wherein the memantine or the pharmaceutically acceptable salt of memantine is present in the pharmaceutical composition in an amount in the range of about 1 mg to about 70 mg.

5. The method of claim 1, wherein:
   the azelastine or the pharmaceutically acceptable salt of azelastine is present in the pharmaceutical composition in an amount in the range of about 10 mg to about 20 mg; and
   the memantine or the pharmaceutically acceptable salt of memantine is present in the pharmaceutical composition in an amount in the range of about 1 mg to about 70 mg.

6. The method of claim 1, further comprising administering the pharmaceutical composition to the patient daily and for a period of at least twelve weeks.

7. The method of claim 1, wherein the pharmaceutical composition comprises about 12 mg to about 20 mg of the azelastine or of the pharmaceutically acceptable salt of azelastine.

8. The method of claim 7, wherein the memantine or the pharmaceutically acceptable salt of memantine is present in the pharmaceutical composition in an amount in the range of about 1 mg to about 70 mg.

9. The method of claim 8, wherein the memantine or the pharmaceutically acceptable salt of memantine is present in the pharmaceutical composition in an amount in the range of about 2 mg to about 30 mg.

10. The method of claim 8, wherein the memantine or the pharmaceutically acceptable salt of memantine is present in the pharmaceutical composition in an amount in the range of about 2 mg to about 5 mg.

11. The method of claim 8, wherein the memantine or the pharmaceutically acceptable salt of memantine is present in the pharmaceutical composition in an amount that is equal to, greater than or less than the amount of the azelastine or of the pharmaceutically acceptable salt of azelastine.

12. The method of claim 8, wherein the azelastine or the pharmaceutically acceptable salt of azelastine is present in the pharmaceutical composition in an amount that is 2, 3, 4, 5, 6, 7, 8, 9, or 10 times as much as the memantine or the pharmaceutically acceptable salt of memantine.

13. The method of claim 1, wherein the memantine or the pharmaceutically acceptable salt of memantine is present in the pharmaceutical composition in an amount in the range of about 2 mg to about 30 mg.

14. The method of claim 1, wherein the memantine or the pharmaceutically acceptable salt of memantine is present in the pharmaceutical composition in an amount in the range of about 2 mg to about 5 mg.

15. The method of claim 1, wherein the memantine or the pharmaceutically acceptable salt of memantine is present in the pharmaceutical composition in an amount that is equal to, greater than or less than the amount of the azelastine or of the pharmaceutically acceptable salt of azelastine.

16. The method of claim 1, wherein the azelastine or the pharmaceutically acceptable salt of azelastine is present in the pharmaceutical composition in an amount of about 12 mg and the memantine or the pharmaceutically acceptable salt of memantine is present in the pharmaceutical composition in an amount of about 5 mg.

17. The method of claim 1, wherein the azelastine or the pharmaceutically acceptable salt of azelastine is present in the pharmaceutical composition in an amount of about 14 mg and the memantine or the pharmaceutically acceptable salt of memantine is present in the pharmaceutical composition in an amount of about 5 mg.

18. The method of claim 1, wherein the azelastine or the pharmaceutically acceptable salt of azelastine is present in the pharmaceutical composition in an amount that is 2, 3, 4, 5, 6, 7, 8, 9, or 10 times as much as the memantine or the pharmaceutically acceptable salt of memantine.

* * * * *